US009089823B2

(12) United States Patent
Trudsoe et al.

(10) Patent No.: US 9,089,823 B2
(45) Date of Patent: Jul. 28, 2015

(54) COLD PREPARED GEL AND METHOD FOR MAKING SAME

(71) Applicant: CP Kelco ApS, Lille Skensved (DK)

(72) Inventors: Jens Eskil Trudsoe, Roskilde (DK); Helle Bech Olsen, Haslev (DK)

(73) Assignee: CP KELCO APS, Lille Skensved (DK)

( * ) Notice: Subject to any disclaimer, the term of this patent is extended or adjusted under 35 U.S.C. 154(b) by 0 days.

(21) Appl. No.: 14/463,078

(22) Filed: Aug. 19, 2014

(65) Prior Publication Data

US 2014/0356317 A1    Dec. 4, 2014

Related U.S. Application Data

(62) Division of application No. 13/077,603, filed on Mar. 31, 2011, now abandoned.

(51) Int. Cl.
| | |
|---|---|
| *B01F 17/00* | (2006.01) |
| *A23L 1/0524* | (2006.01) |
| *A23L 1/09* | (2006.01) |
| *C08J 3/075* | (2006.01) |
| *C08L 5/06* | (2006.01) |
| *A01N 25/04* | (2006.01) |
| *A23L 1/222* | (2006.01) |
| *A61K 47/36* | (2006.01) |
| *C11B 9/00* | (2006.01) |

(52) U.S. Cl.
CPC ............ *B01F 17/0092* (2013.01); *A01N 25/04* (2013.01); *A23L 1/0524* (2013.01); *A23L 1/09* (2013.01); *A23L 1/097* (2013.01); *A23L 1/2225* (2013.01); *A61K 47/36* (2013.01); *C08J 3/075* (2013.01); *C08L 5/06* (2013.01); *C11B 9/00* (2013.01); *A23V 2002/00* (2013.01); *C08J 2305/06* (2013.01)

(58) Field of Classification Search
None
See application file for complete search history.

(56) References Cited

U.S. PATENT DOCUMENTS

| | | | |
|---|---|---|---|
| 4,532,143 | A | 7/1985 | Brain et al. |
| 6,077,557 | A | 6/2000 | Gordon et al. |
| 6,165,534 | A | 12/2000 | Luzio et al. |
| 6,458,405 | B1 | 10/2002 | Roy et al. |
| 6,706,306 | B2 | 3/2004 | Jindra et al. |
| 2008/0032027 | A1 | 2/2008 | Petrella |
| 2008/0057115 | A1 | 3/2008 | Okamoto et al. |
| 2009/0068322 | A1 | 3/2009 | Celhay |

FOREIGN PATENT DOCUMENTS

| | | |
|---|---|---|
| EP | 1 104 652 A1 | 6/2001 |
| WO | 2004/030469 A2 | 4/2004 |

OTHER PUBLICATIONS

Heat and the First Law of Thermodynamics, Chapter 20, (Nov. 4, 2009), pp. 604-610.*
Merriam Webster, Emulsifier, (accessed Feb. 12, 2015), pp. 1-3.*
PCT International Search Report for PCT Application No. PCT/EP2012/053318 mailed May 8, 2012 (4 pages).
PCT Written Opinion of the International Searching Authority for PCT/EP2012/053318 mailed May 8, 2012 (4 pages).
Gomori, G., Preparation of Buffers for Use in Enzyme Studies, General Preparative Procedures, (1955), pp. 138-145.
Byoungseung Yoo, et al., Food Sci. Biotechnol. vol. 12 No. 3 (2003), pp. 316-319.
Cargill, Pectins, (accessed Sep. 17, 2012), p. 1.
Vigalex, Lavender Concrete (Sep. 14, 2007), p. 1.
CountryHome, Almond Pound Cake with Citrus Lavender Glaze, (May 13, 2008), pp. 1-2.
Culinary Lavender, Cooking with Lavender, (Apr. 15, 2008), pp. 1-3.

* cited by examiner

*Primary Examiner* — Scott Long
*Assistant Examiner* — Lyndsey Beckhardt
(74) *Attorney, Agent, or Firm* — Sutherland Asbill & Brennan LLP

(57) ABSTRACT

A gel comprising water, pectin having a DE from about 62 to 75, soluble saccharide or sugar alcohol solids present in an amount from about 44 to 60% by weight of the gel, and a pH reducing agent for reducing the pH of the gel from a level from about 2 to 3. A method for making the gel without heating or cooling is also disclosed.

21 Claims, No Drawings

COLD PREPARED GEL AND METHOD FOR MAKING SAME

CROSS REFERENCE TO RELATED APPLICATIONS

The present application is a divisional of co-pending U.S. application Ser. No. 13/077,603, filed Mar. 31, 2011, which is incorporated herein by reference in its entirety.

TECHNICAL FIELD

This invention relates to gels and more particularly relates to cold prepared gels for use in applications including but not limited to air treatment products or foodstuffs or the like.

BACKGROUND OF THE INVENTION

Gels are used in many applications including foods, such as candies and desserts, and air treatment materials for continuous release of volatile air treatment components such as perfumes, disinfectants, bactericides, insecticidal materials, and the like. Air treatment gels typically comprise an aqueous medium containing the volatile air treatment components and a gel forming matrix. Air treatment gels may be made cold, meaning at about room temperature, and without added heat during mixing of the gel components and the gelling process. Known techniques for making cold prepared air treatment gels are often complex or require expensive, toxic, or hazardous components. Thus, there is a need for cold prepared gels and a method for making such gels that are economical, environment friendly, or even non-toxic or non-hazardous.

BRIEF SUMMARY OF THE INVENTION

This invention addresses one or more of the above-described needs by providing a gel comprising water, pectin having a degree of esterification (DE) from about 62 to about 75, preferably from about 65 to about 75, soluble saccharide or sugar alcohol solids present in an amount from about 44 to about 60%, preferably from about 44 to about 55% by weight of the gel, and a pH reducing agent for reducing the pH of the gel from a level of about 2 to about 3.

According to another aspect of the present invention, a method for preparing a gel is provided comprising forming a gel forming mixture comprising water, pectin having a DE from about 62 to about 75, preferably from about 65 to about 75, soluble saccharide or sugar alcohol solids in an amount from about 44 to about 60%, preferably from about 44 to about 55% by weight of a gel forming mixture, and a pH reducing agent for reducing the pH of the gel forming mixture to a level from about 2 to about 3.

The method the present invention can be carried out without heating the gel forming mixture and the gel forming mixture can be set into a gel without heating or cooling. The resulting gel is relatively stable and remains substantially intact without appreciable syneresis.

Embodiments of this invention are set forth below in the following detailed description and claims.

DETAILED DESCRIPTION OF EMBODIMENTS

As summarized hereinabove, this invention encompasses a gel and a method for making a gel. Several embodiments of this invention are described below including an air treatment gel, although the embodiments of this invention may also be used for other applications such as food products. Parameters of different steps, components, and products of embodiments are described separately, but may be combined consistently with this description and claims to enable still other embodiments as will be understood by those skilled in the art. Through the specification, examples, and claims, unless otherwise indicated, percents are percents by weight.

According to one embodiment of this invention, a gel comprises water, pectin having a DE from about 62 to about 75, preferably from about 65 to about 75, soluble saccharides such as sucrose, glucose, corn sweetener solids and high fructose sweetener or sugar alcohols present in an amount from about 44 to about 60%, preferably from about 44 to about 55% of the weight of the gel and a pH reducing agent for reducing the pH of the gel to a level from about 2 to about 3.

Because pectin is sensitive to metals, the water may be demineralized. According to embodiments of the invention, the water is desirably present in the gel in an amount from about 44 to about 55% by weight of the gel.

According to embodiments of the invention, the pectin is present in the gel in an amount from about 0.5 to about 2.5% by weight of the gel. The use of relatively high DE pectin in the embodiments of this invention provides several advantages over other colloidal materials. For example, pectin costs less than some other colloidals such as carrageenan, is natural, is approved for use in foodstuff, and does not require heating or cooling to form a gel.

According to embodiments of the invention, suitable soluble saccharide solids include monosaccharide and disaccharides such as sucrose, glucose, fructose, ribose, glyceraldehydes, lactose, and maltose. Particularly useful are sucrose and glucose syrup either alone or in combination. When combining sucrose and glucose syrup in a ratio of about 2 parts sucrose and one part glucose syrup, glucose syrup prevents sucrose from crystallizing as the gel evaporates during use. In addition, according to certain embodiments of this invention, suitable soluble sugar alcohol solids include glycerol, erythritol, sorbitol, xylitol, mannitol, lactitol, maltitol, and the like and combinations thereof. Sucrose is particularly suitable as a soluble saccharide solid for use in embodiments of this invention. Combinations of sucrose, glucose, and glycerol are also suitable soluble saccharide and sugar alcohol solids for use in embodiments of this invention. The soluble saccharide or sugar alcohol solids may be present in the gel in an amount from about 44 to about 60% by weight of the gel, or from about 44 to about 55% by weight of the gel according to particular embodiments. If the concentration of soluble saccharide or sugar alcohol solids is above about 60%, the soluble saccharide or sugar alcohol solids will no longer be dissolved unless heat is added. If the concentration of soluble saccharide or sugar alcohol solids is below about 44%, the gel will not form.

According to embodiments of this invention, the pH reducing agent may be a pH reducing acid or salt. According to particular embodiments of the invention, suitable pH reducing agents include citric acid, acetic acid, tartaric acid, malic acid, fumaric acid, lactic acid, salts thereof, and combinations of such acids and salts thereof. The pH reducing agent is present in the gel in a amount sufficient to impart a pH from about 2 to about 3 to the gel. If the pH is higher than about 3, the gel will not form, and if the pH is much below 2, the gel may form too quickly.

According to embodiments of this invention, the gel may also include fragrants, flavorants, colorants, preservatives, and the like.

According to embodiments of the invention, the gel may comprise one or more water immiscible materials dispersed throughout the gel. The water immiscible material may be dispersed in the gel in the form of an emulsion. According to embodiments of the invention, suitable water immiscible materials include a volatile organic component such as an oil or other organic oil immiscible in water or an aqueous matrix. According to embodiments of the invention, suitable water immiscible materials include perfume, flavorant, pheromone, bactericide, insect attractant, insect repellent, animal attractant, animal repellent, insecticide, fungicide, pharmaceutical drug, veterinary drug, and other volatile oils or organic materials.

According to embodiments of the invention, the gel may further comprise an emulsion stabilizer. The emulsion stabilizer may be present in the gel in an amount from about 0.2. to about 1%, preferably from about 0.2 to about 0.5% by weight of the gel according to certain embodiments. According to particular embodiments suitable emulsion stabilizers include sugar beet pectin and the like.

According to an embodiment of this invention, a gel may be made according to a method comprising forming a gel forming mixture comprising water, pectin having a DE from about 62 to about 75, preferably from about 65 to about 75, soluble saccharide or sugar alcohol solids in an amount from about 44 to about 60%, preferably from about 44 to about 55% by weight of the gel forming mixture, and a pH agent for reducing the pH of the gel forming mixture to a level from about 2 to about 3. The gel forming mixture will set into a gel without further processing and without the addition of heat of cooling during mixing or thereafter.

According to another embodiment, a method of forming a gel comprises dissolving a pectin having a DE from about 62 to about 75, preferably from about 65 to about 75 and soluble saccharide or sugar alcohol solids in the water to form a solution, the soluble saccharide or sugar alcohol solids being present in an amount from about 44 to about 60%, preferably from about 44 to about 55% by weight of the gel forming mixture, adding a water immiscible material to the solution, emulsifying the solution, and adding the pH reducing agent to the emulsion. According to particular embodiments, an emulsion stabilizer may also be added and optionally a colorant or preservative or both may be added as well.

According to still another embodiment, a method for forming a gel comprises forming a gel forming mixture comprising the steps of dissolving a pectin having a DE from about 62 to about 75, preferably from about 65 to about 75 and a pH reducing agent in a first portion of water to form a first solution, the pH reducing agent being added in an amount to reduce the pH of the solution to a level from about 2 to about 3, dissolving soluble saccharide or sugar alcohol solids in a second portion of water to form a second solution, the soluble saccharide or sugar alcohol solids being added in an amount of about 44 to about 60%, preferably from about 44 to about 55% by weight of the gel forming mixture, adding a water immiscible material to the second solution, mixing the first and second solution to form a gel forming mixture, and emulsifying the gel forming mixture.

The foregoing embodiments form gels without the addition of heat or cooling. In other words, according to embodiments of the invention, the above described gel forming mixtures may be mixed and form gels at room temperatures. Room temperatures typically range from about 16° C. to about 27° C. In addition, the resulting gels are stable and remain intact without syneresis. Syneresis is the separation of liquid from a gel upon gel formation. Methods for measuring syneresis are known in the art, and include both qualitative and quantitative measurement of the syneresis. For example, the amount of syneresis can be evaluated qualitatively by a visual observation of the liquid separation from a gel. The amount of syneresis can be measured quantitatively by measuring the change in mass in a composition after removal of any liquid that has separated from the gel.

According to embodiments of this invention, the gelling time of the gel forming mixture can be controlled from a few minutes to several hours by varying the DE of the pectin, the amount of soluble saccharide or sugar alcohol solids in the mixture, and the pH of the mixture. For example, the gelling time is longer for lower DE pectin than for higher DE pectin, the gelling time is longer with a lower amount of soluble saccharide or sugar alcohol solids than with a higher amount of the soluble saccharides or sugar alcohol solids, and the gelling time is longer when the gelling mixture has a higher pH than with a lower pH.

In some embodiments, such as those including an emulsion stabilizer like sugar beet pectin, the emulsion stabilizer can slow the release of volatile water immiscible material, such as perfume, in the gel until pressure is applied to the gel. Thus, an emulsion stabilizer such as sugar beet pectin may be used in certain embodiments to provide controlled release of the water immiscible material.

According to certain embodiments, the gel described herein may be liquefied by increasing the pH of the gel to about 3.3 or more.

EXAMPLES

The present invention is further illustrated by the following examples, which are not to be construed in any way as imparting limitations upon the scope thereof. On the contrary, it is to be clearly understood that resort may be had to various other embodiments, modifications, and equivalents thereof which, after reading the description therein, may suggest themselves to those skilled in the art without departing from the scope of the appended claims.

Example 1

Gels were made in accordance with the parameters shown in Table 1 below. Table 1 includes the pectin DE, the amount of pectin in the gel in percent by weight of the gel, the type and amount of soluble saccharide or sugar alcohol solids in the gel in percent by weight of the gel, the amount of pH reducing citric acid in the gel, and the resulting pH of the gel. The objective was to determine the minimal concentration of soluble saccharide or sugar alcohol solids and different pH values. The size of each batch was 400 grams and the gelling time was approximate and was measured in hours. Ten minutes is recorded as 0.10 hours, twenty-five minutes is recorded as 0.25 hours, and so on. The gels were made without the addition of volatile water immiscible materials such as lemon oil or without any colorant.

Demineralized water in an amount sufficient to create a 400 gram batch size was poured into a 2000 liter glass beaker. The pectin was added to the water in the glass beaker along with 5% of the soluble saccharide or sugar alcohol solids. The mixture of pectin and soluble saccharide or sugar alcohol solids was dispersed in the water while stirring for about 20 minutes until the pectin was dissolved. The remaining soluble saccharide or sugar alcohol solids were added to the mixture in the glass beaker and stirring was continued for an additional 20 minutes. The preparation was left standing for 30 minutes to clear air bubbles and citric acid was then added while stirring with a spatula. The preparations with glucose syrup were made by first dissolving the glucose syrup in water and then dispersing pectin in the mixture.

TABLE 1

| Pectin DE | Pectin % | Solid Type | Solid % | Citric Aid % (w/v) | Citric Acid ml | PH | Gel | Gelling Time Hours |
|---|---|---|---|---|---|---|---|---|
| 71 | 1.0 | Sugar | 39 | 20 | 20 | 2.40 | No | NA |
| 71 | 1.0 | Sugar | 39 | 20 | 30 | 2.28 | No | NA |
| 71 | 1.5 | Sugar | 39 | 20 | 30 | 2.28 | No | NA |
| 71 | 2.0 | Sugar | 39 | 20 | 30 | 2.65 | No | NA |
| 71 | 1.0 | Sugar | 39 | 60 | 10 | 2.27 | No | NA |
| 71 | 1.0 | Sugar | 39 | 60 | 20 | 2.04 | No | NA |
| 71 | 1.0 | Sugar | 44 | 20 | 10 | 2.73 | Yes | 16 |
| 71 | 1.0 | Sugar | 44 | 20 | 20 | 2.45 | Yes | 16 |
| 71 | 1.0 | Sugar | 44 | 40 | 10 | 2.29 | Yes | 16 |
| 71 | 1.0 | Sugar | 44 | 40 | 20 | 2.17 | Yes | 16 |
| 71 | 1.0 | Sugar | 49 | 20 | 10 | 2.71 | Yes | 2 |
| 71 | 1.0 | Sugar | 49 | 20 | 20 | 2.44 | Yes | 1 |
| 71 | 1.0 | Sugar | 49 | 20 | 30 | 2.25 | Yes | 1 |
| 71 | 1.0 | Sugar | 49 | 40 | 20 | 2.14 | Yes | 0.40 |
| 71 | 0.75 | Sugar | 49 | 20 | 20 | 2.41 | Yes | 1.30 |
| 71 | 1.0 | Sugar | 54 | 20 | 5 | 2.97 | Yes | 0.25 |
| 71 | 1.0 | Sugar | 54 | 20 | 10 | 2.68 | Yes | 0.15 |
| 71 | 1.0 | Sugar | 54 | 20 | 20 | 2.33 | Yes | 0.05 |
| 71 | 0.75 | Sugar | 54 | 20 | 20 | 2.38 | Yes | 0.05 |
| 71 | 1.0 | Glycerin | 49 | 20 | 20 | 2.59 | Yes | 0.10 |
| 71 | 1.0 | Glucose | 49 | 40 | 20 | 2.07 | Yes | 0.05 |
| 66 | 1.0 | Sugar | 49 | 20 | 20 | 2.42 | Yes | 1.15 |

Table 1 shows that gelation takes place when the sugar level is in the range from about 44% to about 55% by weight of the gel and the pH of the gel is in the range from about 2 to 3. In addition, Table 1 shows that gelation occurs with sugar, glycerol, and glucose syrup. With these parameters, the gelling time can be controlled from about 16 hours to about 5 minutes. Table 1 also shows that gelling takes place faster with a pectin product having a higher degree of esterification. It is to be noted that the same gels were made first by dissolving pectin and acid in water then dissolving the sugar and the pectin-at acid mixture.

Example 2

Another set of pectin gels was made in accordance with the parameters set forth in Table 2. In these experiments, the objective was the follow the development of the gel strengths over time. Different solid concentrations and pHs were investigated. The batch size was 1200 grams. The break strength is the force needed to break the gel and the gel strength is the force needed to deform the gel by 2 millimeters. The gels were made without the addition of any volatile water immiscible material dispersed in the gel or any colorant.

Table 2 includes the pectin DE, the amount of pectin in the gel in percent by weight of the gel, the type and amount of soluble saccharide or sugar alcohol solids in the gel in percent by weight of the gel, the pH of the gel, and the gelation time in hours. Again, 30 minutes is shown as 0.30 hours, 40 minutes is shown as 0.40 hours, and so on.

Demineralized water was poured into a 2000 milliliter glass beaker in an amount sufficient to make a 1200 gram batches. Pectin was mixed with 5% of the soluble saccharide or sugar alcohol solids, and the mixture of pectin and soluble saccharide or sugar alcohol solids was dispersed in the water in the beaker while stirring for about 20 minutes until the pectin was dissolved. The remaining soluble saccharide or sugar alcohol solids were added and stirring was continued for an additional 20 minutes. The preparation was left standing for 30 minutes to clear air bubbles and the citric acid was added while stirring with a spatula. Again, the preparations with glucose syrup were made by first dissolving the glucose syrup in water and then dispersing pectin in the mixture.

The break strength of a gel is defined as the load needed to break the gel, while the gel strength of a gel is defined as the load required to deform the gel by 2 mm.

After having added the acid and distributed the acid in the solution, the liquid was poured into crystallizing dishes having diameter of about 70 mm and height of about 40 mm and having adhesive tape attached to the rim allowing filling to about 5 mm above the rim of the crystallizing dish. Before measuring break strength and gel strength, the gel was cut level with the brim using a wire cheese cutter. At room temperature, the crystallizing dish was placed on Texture Analyzer TA.XT.Plus from Stable Micro Systems, equipped with a one half inch plunger, which was driven through the gel with a speed of 1 mm per second.

TABLE 2

| Pectin DE | Pectin % | Solid Type | Solid % | PH | Time Hours | Break Strength Grams | Gel Strength Grams | Comments |
|---|---|---|---|---|---|---|---|---|
| 66 | 1.0 | Sugar | 50 | 2.21 | 24 | 33.341 | 6.625 | Dry, cohesive |
| | | | | | 31 | 50.859 | 9.354 | Dry, cohesive |
| | | | | | 48 | 126.299 | 17.338 | Dry, cohesive |
| | | | | | 72 | 174.631 | 25.087 | Dry, cohesive |
| 66 | 1.0 | Sugar | 55 | 2.31 | 0.30 | 152.004 | 18.439 | Dry, cohesive |
| | | | | | 1 | 217.607 | 28.063 | Dry, cohesive |
| | | | | | 3 | 262.851 | 38.529 | Dry, cohesive |
| | | | | | 24 | 329.162 | 54.194 | Dry, cohesive |

TABLE 2-continued

| Pectin DE | Pectin % | Solid Type | Solid % | PH | Time Hours | Break Strength Grams | Gel Strength Grams | Comments |
|---|---|---|---|---|---|---|---|---|
| 71 | 1.0 | Sugar | 50 | 2.21 | 0.40 | 84.941 | 12.746 | Dry, cohesive |
|  |  |  |  |  | 2 | 167.95 | 34.823 | Dry, cohesive |
|  |  |  |  |  | 3 | 227.006 | 39.596 | Dry, cohesive |
|  |  |  |  |  | 24 | 344.827 | 66.681 | Dry, cohesive |
|  |  |  |  |  | 48 | 403.153 | 71.139 | Dry, cohesive |
| 71 | 1.0 | Sugar | 55 | 2.39 | 0.08 | 131.162 | 16.249 | Dry, cohesive |
|  |  |  |  |  | 0.30 | 273.362 | 46.041 | Dry, cohesive |
|  |  |  |  |  | 2 | 388.622 | 66.064 | Dry, cohesive |
|  |  |  |  |  | 4 | 356.427 | 71.634 | Dry, cohesive |
|  |  |  |  |  | 24 | 462.917 | 86.108 | Dry, cohesive |
|  |  |  |  |  | 48 | 445.231 | 92.869 | Dry, cohesive |
| 71 | 1.5 | Sugar | 50 | 2.48 | 1 | 116.058 | 19.91 | Dry, cohesive |
|  |  |  |  |  | 3 | 205.715 | 45.659 | Dry, cohesive |
|  |  |  |  |  | 5 | 273.306 | 68.321 | Dry, cohesive |
|  |  |  |  |  | 24 | 420.031 | 118.203 | Dry, cohesive |
|  |  |  |  |  | 100 | 554.674 | 136.114 | Dry, cohesive |
| 71 | 0.5 | Sugar | 50 | 2.28 | 5 | 22.717 | 6.064 | Dry, cohesive |
|  |  |  |  |  | 7 | 36.912 | 7.849 | Dry, cohesive |
|  |  |  |  |  | 24 | 89.421 | 14.475 | Dry, cohesive |
|  |  |  |  |  | 100 | 122.964 | 20.292 | Dry, cohesive |
| 71 | 1.0 | Glycerin | 50 | 2.42 | 0.20 | 184.266 | 30.848 | Dry, cohesive |
|  |  |  |  |  | 1 | 244.558 | 44.716 | Dry, cohesive |
|  |  |  |  |  | 2 | 281.391 | 52.88 | Dry, cohesive |
|  |  |  |  |  | 5 | 331.655 | 58.27 | Dry, cohesive |
|  |  |  |  |  | 24 | 355.158 | 62.369 | Dry, cohesive |
| 71 | 1.0 | Glucose | 50 | 2.39 | 0.15 | 162.93 | 37.99 | Dry, cohesive |
|  |  |  |  |  | 0.55 | 194.193 | 54.25 | Dry, cohesive |
|  |  |  |  |  | 3 | 178.988 | 55.081 | Dry, cohesive |
|  |  |  |  |  | 6 | 341.469 | 56.53 | Dry, cohesive |
|  |  |  |  |  | 24 | 487.117 | 51.903 | Dry, cohesive |
| 71 | 1.0 | Sugar | 55 | 2.74 | 0.40 | 175.597 | 20.18 | Dry, cohesive |
|  |  |  |  |  | 2 | 354.091 | 43.93 | Dry, cohesive |
|  |  |  |  |  | 4 | 441.592 | 55.575 | Dry, cohesive |
|  |  |  |  |  | 7 | 345.983 | 60.842 | Dry, cohesive |
|  |  |  |  |  | 24 | 370.273 | 74.811 | Dry, cohesive |
|  |  |  |  |  | 106 | 508.655 | 86.21 | Dry, cohesive |

Table 2 shows the development over time of the break strength and the gel strength of gels made with a slow set pectin and a rapid set pectin. A slow set pectin is characterized by having a degree of esterification in the range from about 58 to about 67, whereas a rapid set pectin is characterized by a degree of esterification higher than about 68. In the pH range of 2.2 to 2.4, both break strength and gel strength of a slow set pectin gel increased with increasing sheering concentration and the gel developed faster with higher sugar concentration. The same is seen for the rapid set pectin, which also provided for higher strengths than the slow set pectin. In addition, the rapid set pectin gel developed faster than the slow set pectin gel, particularly at the lower concentration of sugar.

In addition, Table 2 shows that the pH can apparently be varied somewhat without any major change in gel strengths. Furthermore, both the break strength and gel strength increase with increased pectin concentration. At 0.5% pectin, the time of the development of the gel was relatively long, and the optimum concentration appeared to be about 1% by weight of the gel. The gel strength did not change according to the type of soluble solids employed. With respect to break strength, glucose provided for the highest value, whereas glycerol appeared to faster develop the gel than sugar. However, all three soluble saccharides or sugar alcohols provided adequate gelation.

Example 3

One pectin gel was made with heat and one was made without heat to compare the effective heating on the gel. Table 3 discloses the parameters according to which the gels were made including the heat, the pectin DE, the percent by weight of pectin in the gel, the type and percent by weight of the soluble saccharide (sugar) solids in the gel, the pH of the gel, and the gelling time in hours. Again, in Table 3, 40 minutes is shown as 0.40 hours.

The gels were made by first pouring demineralized water into a 2000 millimeter glass beaker to make a total batch size 1200 grams for each gel. The pectin was mixed with 5% of the sugar in the mixture of pectin and sugar was dispersed in the water while stirring for about 20 minutes while the pectin was dissolved. The remaining sugar was added and stirring was continued for an additional 20 minutes. The preparation was left standing to clear any air bubbles and citric acid was added while stirring with a spatula. The heated gel was made by heating the solution of pectin and sugar in water for 5 minutes at 85° C.

TABLE 3

| Heat | Pectin DE | Pectin % | Solid Type | Solid % | PH | Time Hours | Break Strength Grams | Gel Strength Grams |
|---|---|---|---|---|---|---|---|---|
| None | 71 | 1.0 | Sugar | 50.0 | 2.21 | 0.40 | 84.941 | 12.746 |
|  |  |  |  |  |  | 2 | 167.95 | 34.823 |
|  |  |  |  |  |  | 3 | 227.006 | 39.596 |
|  |  |  |  |  |  | 24 | 344.827 | 66.681 |
|  |  |  |  |  |  | 48 | 403.153 | 71.139 |
| 85° C. | 71 | 1.0 | Sugar | 50.0 | 2.39 | 2 | 78.124 | 13.532 |
|  |  |  |  |  |  | 4 | 138.427 | 27.647 |
|  |  |  |  |  |  | 24 | 236.708 | 54.441 |

TABLE 3-continued

| Heat | Pectin DE | Pectin % | Solid Type | Solid % | PH | Time Hours | Break Strength Grams | Gel Strength Grams |
|---|---|---|---|---|---|---|---|---|
|  |  |  |  |  |  | 48 | 310.363 | 62.01 |
|  |  |  |  |  |  | 106 | 366.298 | 77.697 |

Table 3 shows that heating apparently leads to lower break strength over time, whereas the gel strength appears to be unaffected by heat.

Example 4

In this experiment, the effect of freezing a gel and subsequently thawing was investigated. The objective was to visually determine if any syneresis occurred during thawing. The gels were made without addition of any volatile water immiscible material such as lemon oil and without any colorant. 79 grams of glucose syrup (TS 84%) was weighed in a 2000 milliliter glass beaker. 185 grams of demineralized water were added to the beaker and the mixture was stirred for about 20 minutes until the glucose syrup was dissolved. 4 grams of pectin having a DE of 71 was mixed with about 5 grams of sugar and dispersed into the mixture of demineralized water and glucose syrup. The dispersion was stirred for about 20 minutes until the pectin was dissolved. 98 grams of sugar along with 1 milliliter of 28% sodium benzoate were added to the mixture and stirring continued for about 20 minutes until the sugar was dissolved. 20 milliliters of 20% citric acid were then added to the mixture while stirring with a spatula. The resulting gel was completely dry with no syneresis and was freeze thaw stable.

Example 5

The effective of the additional of sugar beet pectin was observed. Several gels were made with no sugar beet pectin, 0.25% by weight sugar beet pectin, and 0.50% by weight sugar beet pectin.

76 grams of glucose syrup (TS 84%) was weighed in a 2000 milliliter glass beaker. 168 grams of demineralized water was added to the beaker and the mixture was stirred for about 20 minutes until the glucose syrup was dissolved. 4 grams of pectin having a DE of 71 was mixed with about 6 grams of sugar and dispersed into the mixture of demineralized water and glucose syrup. The dispersion was stirred for about 20 minutes until the pectin was dissolved. 120 grams of sugar was added to the mixture and stirring continued for about 20 minutes until the sugar was dissolved. The preparation was left standing for 20 minutes to clear air bubbles and a colorant was added. Except for the gels made without sugar beet pectin, the sugar beet pectin was dispersed in lemon oil and added to the mixture while stirring on high speed. For the gel without sugar beet pectin, lemon oil was added to the mixture while stirring on high speed. 1 milliliter of 20% sodium benzoate preservative was also added and the preparation was emulsified with a Silverson L4R high speed mixer for 4 minutes. Before citric acid was added to the emulsion, samples of the gelling mixture were taken to observe oil droplets sizes over time.

The gel with no sugar beet pectin had an oil droplet size of about 10 microns from the start of the storage period. The gel made with 0.25% by weight of sugar beet pectin produced oil droplets generally smaller than the gel without the sugar beet pectin. However, with more storage time, the oil droplets increased in size but were still about half the size as the oil droplets in the gel made without sugar beet pectin. The gel made with 0.5% by weight sugar beet pectin had an oil droplet size that was very small and remained very small for at least 24 hours. It was noticed that even with small concentrations of sugar beet pectin, the scent of lemon oil was reduced, however, when one applied pressure on the gel, the scent was released.

Example 6

Melting of a pectin gel was observed. First a pectin gel was made by adding 200 grams of demineralized water into a 2000 milliliter glass beaker. 4 grams of pectin having a DE of 71 were mixed with about 10 grams of sugar. The mixture of pectin sugar was dispersed in the water in the beaker while stirring for about 20 minutes until the pectin was dissolved. 186 grams of sugar were then added to the mixture in the beaker and along with 1 milliliter of 20% sodium benzoate and stirring was continued for an additional 20 minutes. The preparation was left standing for 30 minutes to clear air bubbles and then 20 milliliters of 20% citric acid were added while stirring with a spatula. The gel was set and the pH was measured to be about 2.35. The gel was disrupted with a propeller stirrer and the pH was increased to 3.29 with the sodium hydroxide and the gel melted.

It should be understood that the foregoing relates only to the preferred embodiments of the present application and that numerous changes and modifications may be made herein without departing from the general scope of the invention as defined by the following claims and the equivalents thereof.

We claim:

1. A method for preparing a gel, the method comprising:
   forming a gel forming mixture at a temperature, the gel forming mixture comprising:
      water;
      a pectin having a degree of esterification from about 62 to about 75;
      a soluble saccharide or sugar alcohol solids in an amount from about 44 to about 60% by weight of the gel forming mixture; and
      a pH reducing agent for reducing the pH of the gel forming mixture to a level from about 2 to about 3,
   wherein the gel forming mixture forms the gel, and
   wherein the temperature is substantially maintained during the method for preparing the gel.

2. The method of claim 1, further comprising adding a water immiscible material to the gel forming mixture.

3. The method of claim 2, further comprising emulsifying the gel forming mixture.

4. The method of claim 2, wherein the step of forming the gel forming mixture comprises:
   dissolving the pectin and soluble saccharide or sugar alcohol solids in the water to form a solution;
   adding the water immiscible material to the solution;
   emulsifying the solution; and
   adding the pH reducing agent to the emulsion.

5. The method of claim 2, wherein the step of forming the gel forming mixture comprises:
   dissolving the pectin and the pH reducing agent in a first portion of the water to form a first solution;
   dissolving the soluble saccharide or sugar alcohol solids in a second portion of the water to form a second solution;
   adding the water immiscible material to the second solution;
   mixing the first and second solutions to form the gel forming mixture; and
   emulsifying the gel forming mixture.

6. The method of claim 1, wherein the pectin is present in the gel in an amount from about 0.5 to about 2.5% by weight of the gel.

7. The method of claim 1, wherein the soluble saccharide or sugar alcohol solids are selected from the group consisting of sucrose, glucose, fructose, ribose, glyceraldehyde, lactose, maltose, glycerol, erythritol, sorbitol, xylitol, mannitol, lactitol, maltitol, and combinations thereof.

8. The method of claim 1, wherein the soluble saccharide or sugar alcohol solids comprise sucrose.

9. The method of claim 1, wherein the soluble saccharide or sugar alcohol solids comprise sucrose, glucose, and glycerol.

10. The method of claim 1, wherein the pH reducing agent is an acid or salt.

11. The method of claim 1, wherein the pH reducing agent is selected from the group consisting of citric acid, acetic acid, tartaric acid, malic acid, fumaric acid, lactic acid, salts thereof, and combinations of said acids and salts.

12. The method of claim 2, wherein the water immiscible material comprises a perfume, flavorant, pheromone, bactericide, insect attractant, insect repellant, animal attractant, animal repellant, insecticide, fungicide, pharmaceutical drug, veterinary drug, or combinations thereof.

13. The method of claim 2, wherein the gel forming mixture further comprises an emulsion stabilizer.

14. The method of claim 13, wherein the emulsion stabilizer is present in the gel in an amount from about 0.2 to about 0.5% by weight of the gel.

15. The method of claim 13, wherein the emulsion stabilizer comprises a sugar beet pectin.

16. The method of claim 1, wherein the water is demineralized.

17. The method of claim 1, wherein the water is in an amount from 44 to about 55% by weight of the gel.

18. The method of claim 1, wherein the pectin has a degree of esterification from about 65 to about 75.

19. The method of claim 1, wherein the temperature is from about 16° C. to about 27° C.

20. The method of claim 1, wherein the temperature is about room temperature.

21. A method for preparing a gel, the method comprising:
forming a gel forming mixture at a first temperature from about 16° C. to about 27° C., the gel forming mixture comprising:
water;
a pectin having a degree of esterification from about 62 to about 75;
a soluble saccharide or sugar alcohol solids in an amount from about 44 to about 60% by weight of the gel forming mixture; and
a pH reducing agent for reducing the pH of the gel forming mixture to a level from about 2 to about 3,
wherein the gel forming mixture forms the gel at a second temperature from about 16° C. to about 27° C.

* * * * *